US008691863B2

(12) United States Patent
Fischer et al.

(10) Patent No.: US 8,691,863 B2
(45) Date of Patent: Apr. 8, 2014

(54) USE OF ACTIVE SUBSTANCE COMBINATIONS HAVING INSECTICIDAL PROPERTIES FOR CONTROLLING ANIMAL PESTS FROM THE STINK BUG FAMILY

(75) Inventors: Reiner Fischer, Monheim (DE); Konrad Kemper, Sao Paulo (BR); Jürgen Kühnhold, Bergisch Gladbach (DE); Xavier Alain Marie Van Waetermeulen, Morancé (FR); Francisco Leonel Junior Lozano, Sao Paulo (BR)

(73) Assignee: Bayer CropScience AG, Monheim (DE)

( * ) Notice: Subject to any disclaimer, the term of this patent is extended or adjusted under 35 U.S.C. 154(b) by 499 days.

(21) Appl. No.: 12/665,674

(22) PCT Filed: Jun. 17, 2008

(86) PCT No.: PCT/EP2008/004849
§ 371 (c)(1),
(2), (4) Date: May 25, 2010

(87) PCT Pub. No.: WO2009/000443
PCT Pub. Date: Dec. 31, 2008

(65) Prior Publication Data
US 2010/0240643 A1   Sep. 23, 2010

(30) Foreign Application Priority Data

Jun. 28, 2007 (EP) .................................. 07111269

(51) Int. Cl.
| *A01N 43/38* | (2006.01) |
| *A61K 31/40* | (2006.01) |
| *A01N 43/12* | (2006.01) |
| *A01N 43/26* | (2006.01) |
| *A61K 31/34* | (2006.01) |
| *A61K 31/335* | (2006.01) |

(52) U.S. Cl.
USPC .......................................... 514/409; 514/462

(58) Field of Classification Search
USPC ................................................ 514/409, 462
See application file for complete search history.

(56) References Cited

U.S. PATENT DOCUMENTS

| 4,742,060 | A | 5/1988 | Shiokawa et al. | |
| 4,849,432 | A | 7/1989 | Shiokawa et al. | |
| 5,852,012 | A | 12/1998 | Maienfisch et al. | |
| 6,114,374 | A | 9/2000 | Lieb et al. | |
| 6,218,407 | B1* | 4/2001 | Erdelen et al. | 514/341 |
| 6,423,726 | B2* | 7/2002 | Dutzmann et al. | 514/341 |
| 6,864,276 | B2* | 3/2005 | Fischer et al. | 514/409 |
| 7,638,547 | B2* | 12/2009 | Himmler et al. | 514/409 |
| 2003/0148999 | A1 | 8/2003 | Fischer et al. | |
| 2003/0212086 | A1* | 11/2003 | Fischer et al. | 514/279 |
| 2004/0023959 | A1 | 2/2004 | Fischer et al. | |
| 2004/0038827 | A1 | 2/2004 | Fischer et al. | |
| 2004/0044066 | A1 | 3/2004 | Fischer et al. | |
| 2004/0102326 | A1 | 5/2004 | Fischer et al. | |
| 2005/0187107 | A1* | 8/2005 | Smith et al. | 504/100 |
| 2007/0032539 | A1 | 2/2007 | Himmler | |
| 2007/0265266 | A1 | 11/2007 | Fischer et al. | |
| 2007/0270416 | A1 | 11/2007 | Funke et al. | |
| 2008/0287435 | A1 | 11/2008 | Fischer et al. | |
| 2009/0298903 | A1 | 12/2009 | Fischer et al. | |
| 2010/0168090 | A1 | 7/2010 | Fischer et al. | |

FOREIGN PATENT DOCUMENTS

| DE | 103 42 673 A1 | 4/2005 |
| EP | 0 302 389 A2 | 2/1989 |
| EP | 0 376 279 A2 | 7/1990 |
| EP | 0 649 845 A1 | 4/1995 |
| WO | WO 91/04965 A1 | 4/1991 |
| WO | WO 01/89300 A1 | 11/2001 |
| WO | WO 02/05648 A1 | 1/2002 |
| WO | WO 2004/007448 A1 | 1/2004 |
| WO | WO 2007/131681 A2 | 11/2007 |
| WO | WO 2008/006516 A1 | 1/2008 |

OTHER PUBLICATIONS

Bauer, T.A., et al., "Response of Selected Weed Species to Postemergence Imazethapyr and Bentazon," *Weed Tech.* 9:236-242, The Weed Science Society of America (1995).
Blackshaw, R.E., "HOE-39866 Use in Chemical Fallow Systems," *Weed Tech.* 3:420-428, The Weed Science Society of America (1989).
Blackshaw, R.E., "Synergistic Mixes of DPX-A7881 and Clopyralid in Canola (*Brassica napus*)," *Weed Tech.* 3:690-695, The Weed Science Society of America (1989).
Blackshaw, R.E., et al., "Herbicide Combinations for Postemergent Weed Control in Safflower (*Carthamus tinctorius*)," *Weed Tech.* 4:97-104, The Weed Science Society of America (1990).
Blouin, D.C., et al., "Analysis of Synergistic and Antagonistic Effects of Herbicides Using Nonlinear Mixed-Model Methodology," *Weed Tech.* 18:464-472, The Weed Science Society of America (2004).
Bradley, P.R., et al., "Response of Sorghum (*Sorghum bicolor*) to Atrazine, Ammonium Sulfate, and Glyphosate," *Weed Tech.* 14:15-18, The Weed Science Society of America (2000).
Buker, III, R.S., et al., "Confirmation and Control of a Paraquat-Tolerant Goosegrass (*Eleusine indica*) Biotype," *Weed Tech.* 16:309-313, The Weed Science Society of America (2002).
Burke, I.C., et al., "CGA-362622 Antagonizes Annual Grass Control with Clethodim," *Weed Tech.* 16:749-754, The Weed Science Society of America (2002).
Colby, S.R., "Calculating Synergistic and Antagonistic Responses of Herbicide Combinations," *Weeds* 15:20-22, Weed Science Society of America (1967).
Flint, J.L., et al., "Analyzing Herbicide Interactions, A Statistical Treatment of Colby's Method," *Weed Tech.* 2:304-309, The Weed Science Society of America (1988).
Gillespie, G.R., and Nalewaja, J.D., "Wheat (*Triticum aestivum*) Response to Triallate Plus Chlorsulfuron," *Weed Tech.* 3:20-23, The Weed Science Society of America (1989).

(Continued)

*Primary Examiner* — Anna Pagonakis
(74) *Attorney, Agent, or Firm* — Sterne, Kessler, Goldstein & Fox, P.L.L.C.

(57) ABSTRACT

The present invention relates to the use of active substance combinations which consist firstly of known cyclic ketoenols and secondly of further known insecticidal active substances, for controlling animal pests from the stink bug family (Pentatomidae).

7 Claims, No Drawings

(56) References Cited

OTHER PUBLICATIONS

Green, J.M., et al., "Metribuzin and Chlorimuron Mixtures for Preemergence Broadleaf Weed Control in Soybeans, *Glycine max*," *Weed Tech.* 2:355-363, The Weed Science Society of America (1988).

Harker, K.N., and O'Sullivan, P.A., "Synergistic Mixtures of Sethoxydim and Fluazifop on Annual Grass Weeds," *Weed Tech.* 5:310-316, The Weed Science Society of America (1991).

Kent, L.M., et al., "Effect of Ammonium Sulfate, Imazapyr, and Environment on the Phytotoxicity of Imazethapyr," *Weed Tech.* 5:202-205, The Weed Science Society of America (1991).

Kotoula-Syka, E., et al., "Interactions between SAN 582H and Selected Safeners on Grain *Sorghum* (*Sorghum bicolor*) and Corn (*Zea mays*)," *Weed Tech.* 10:299-304, The Weed Science Society of America (1996).

Lanclos, D.Y., et al., "Glufosinate Tank-Mix Combinations in Glufosinate-Resistant Rice (*Oryza sativa*)," *Weed Tech.* 16:659-663, The Weed Science Society of America (2002).

Norris, J.L., et al., "Weed Control from Herbicide Combinations with Three Formulations of Glyphosate," *Weed Tech.* 15:552-558, The Weed Science Society of America (2001).

Novosel, K.M., et al., "Metolachlor Efficacy as Influenced by Three Acetolactate Synthase-Inhibiting Herbicides," *Weed Tech.* 12:248-253, The Weed Science Society of America (1998).

Palmer, E.W., et al., "Broadleaf Weed Control in Soybean (*Glycine max*) with CGA-277476 and Four Postemergence Herbicides," *Weed Tech.* 14:617-623, The Weed Science Society of America (2000).

Rummens, F.H.A., "An Improved Definition of Synergistic and Antagonistic Effects," *Weed Science* 23(1):4-6, The Weed Science Society of America, United States (1975).

Salzman, F.P., and Renner, K.A., "Response of Soybean to Combinations of Clomazone, Metribuzin, Linuron, Alachlor, and Atrazine," *Weed Tech.* 6:922-929, The Weed Science Society of America (1992).

Scott, R.C., et al., "Spray Adjuvant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America (1998).

Shaw, D.R. and Arnold, J.C., "Weed Control from Herbicide Combinations with Glyphosate," *Weed Tech.* 16:1-6, The Weed Science Society of America (2002).

Snipes, C.E., and Allen, R.L., "Interaction of Graminicides Applied in Combination Pyrithiobac," *Weed Tech.* 10:889-892, The Weed Science Society of America (1996).

Sun, Y.-P. & Johnson, E.R., "Analysis of Joint Action of Insecticides Against House Flies", *J. Econ. Entomol.* 53:887-892, United States (1960).

Tammes, P.M.L., "Isoboles, A Graphic Representation of Synergism in Pesticides," *Neth. J. Plant Path.* 70:73-80, Springer, Germany (1964).

Wehtje, G. and Walker, R.H., "Interaction of Glyphosate and 2,4-DB for the Control of Selected Morningglory (*Ipomoea* spp.) Species," *Weed Tech.* 11:152-156, The Weed Science Society of America (1997).

Zhang, W., et al., "Fenoxaprop Interactions for Barnyardgrass (*Echinochloa crus-galli*) Control in Rice," *Weed Tech.* 19:293-297, The Weed Science Society of America (2005).

Accession No. 2005-559271, Database WPI, Section Ch, Week 200557, Thomson Scientific, London, Great Britain, Aug. 11, 2005.

English language Abstract of German Patent Publication No. DE 103 42 673 A1, European Patent Office, European Patent Office, Espacenet database—Worldwide (2005).

English language translation of WIPO Patent Publication No. WO 02/05648 A1.

International Search Report for International Application No. PCT/EP2008/004849, European Patent Office, Rijswijk, Netherlands, mailed on Aug. 11, 2009.

Office Action of co-pending U.S. Appl. No. 10/520,549, § 371(c) Date: Mar. 9, 2006, U.S. Patent and Trademark Office, Alexandria, VA, mailed May 12, 2009.

* cited by examiner

USE OF ACTIVE SUBSTANCE COMBINATIONS HAVING INSECTICIDAL PROPERTIES FOR CONTROLLING ANIMAL PESTS FROM THE STINK BUG FAMILY

The present invention relates to the use of active substance combinations which consist firstly of known cyclic ketoenols and secondly of further known insecticidal active substances, for controlling animal pests from the stink bug family (Pentatomidae).

It is already known that certain cyclic ketoenols have herbicidal, insecticidal and acaricidal properties. While the activity of these substances is good, it leaves something to be desired in some cases at low application rates.

It is known that 1H-3-arylpyrrolidine-2,4-dione derivatives (WO 98/05638) and their cis isomers (WO 04/007448) have insecticidal and/or acaricidal activity.

Also known are mixtures of compounds from WO 98/05638 with other insecticides and/or acaricides: WO 01/89300, WO 02/00025, WO 02/05648, WO 02/17715, WO 02/19824, WO 02/30199, WO 02/37963, WO 05/004603, WO 05/053405, WO 06/089665, DE-A-10342673 and WO 2008/006516. However, the activity of these mixtures is not always satisfactory.

The activity against plant bugs (family: Miridae) (WO 2007/131681) is also known.

It has now been found that active substance combinations comprising compounds of the formulae (I-1) or (I-2)

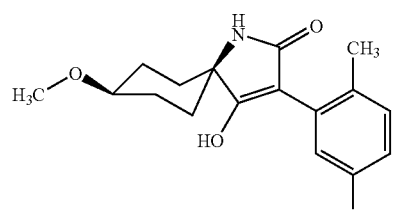
(I-1)

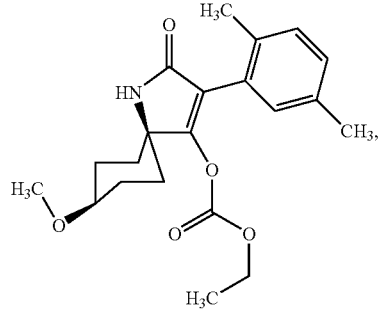
(I-2)

both compounds being known from WO 04/007448,
and at least one acetylcholine receptor agonist or antagonist,
in particular a compound of the following formulae:

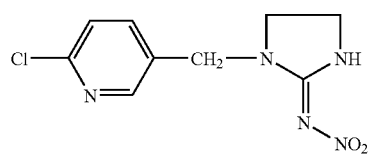 [SMILES: O=[N+]([O-])/N=C1\NCCN1Cc1ccc(Cl)nc1]

imidacloprid (A1), disclosed in EP-A-00192060
and/or

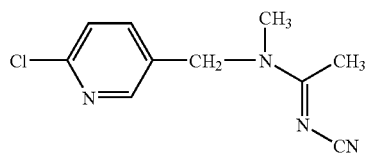

acetamiprid (A2), disclosed in WO 91/04965
and/or

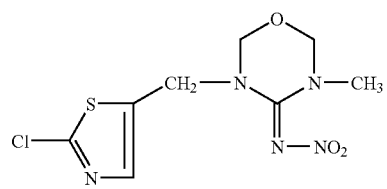 [SMILES: CN1COCN(Cc2cnc(Cl)s2)/C1=N/[N+](=O)[O-]]

thiamethoxam (A3), disclosed in EP-A-00580553
and/or

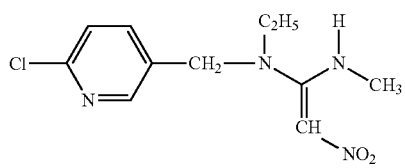 [SMILES: CCN(Cc1ccc(Cl)nc1)/C(=C/[N+](=O)[O-])NC]

nitenpyram (A4), disclosed in EP-A-00302389
and/or

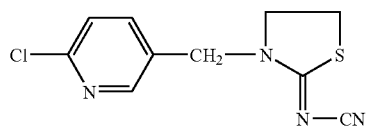

thiacloprid (A5), disclosed in EP-A-00235725
and/or

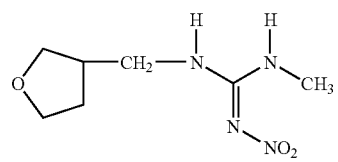

dinotefuran (A6), disclosed in EP-A-00649845
and/or

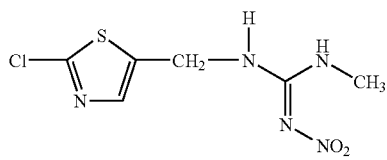

clothianidin (A7), disclosed in EP-A-00376279 and/or

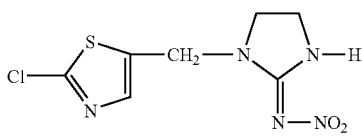

imidaclothiz (A8), disclosed in EP A 00192060 are particularly well suited for controlling insects from the stink bug family (Pentatomidae) in crops such as soybeans, cotton, maize, rice and cereals.

Surprisingly, the insecticidal activity of the active substance combinations according to the invention against stink bugs from the Pentatomidae family is considerably higher than the sum of the activities of the individual active substances. A true synergistic effect which could not have been predicted exists, not simply a complementation of action.

Preferred active substance combinations are those comprising the compounds of the formula (I-1) and at least one active substance from the group of the acetylcholine receptor agonists or antagonists.

Also preferred active substance combinations are those comprising the compound of the formula (I-2) and at least one active substance from the group of the acetylcholine receptor agonists or antagonists.

The following combinations are of particular interest: (I-1)+(A1), (I-1)+(A2), (I-1)+(A3), (I-1)+(A4), (I-1)+(A5), (I-1)+(A6), (I-1)+(A7), (I-1)+(A8), (I-2)+(A1), (I-2)+(A2), (I-2)+(A3), (I-2)+(A4), (I-2)+(A5), (I-2)+(A6), (I-2)+(A7), (I-2)+(A8).

Moreover, the active substance combinations may also comprise further fungicidally, acaricidally or insecticidally active admixture components.

The improved activity is particularly obvious when the active substances are present in certain weight ratios in the active substance combinations according to the invention. However, the weight ratios of the active substances in the active substance combinations may be varied within a relatively wide range. In general, the combinations according to the invention comprise active substances of the formula (I-1) or (I-2) and the mixing partner in the preferred and especially preferred mixing ratios which are detailed in the table hereinbelow:

the mixing ratios are based on weight ratios. The ratio should be interpreted as active substance of the formula (I-1):mixing partner or formula (I-2):mixing partner

| Mixing partner | Preferred mixing ratio | Especially preferred mixing ratio | Very especially preferred mixing ratio |
|---|---|---|---|
| Imidacloprid | 25:1 to 1:25 | 5:1 to 1:5 | 3:1 to 1:3 |
| Acetamiprid | 25:1 to 1:25 | 5:1 to 1:5 | 3:1 to 1:3 |
| Thiamethoxam | 25:1 to 1:25 | 5:1 to 1:5 | 3:1 to 1:3 |
| Nitenpyram | 25:1 to 1:25 | 5:1 to 1:5 | 3:1 to 1:3 |
| Thiacloprid | 25:1 to 1:25 | 5:1 to 1:5 | 3:1 to 1:3 |
| Dinotefuran | 25:1 to 1:25 | 5:1 to 1:5 | 3:1 to 1:3 |
| Clothianidin | 25:1 to 1:25 | 5:1 to 1:5 | 3:1 to 1:3 |
| Imidaclothiz | 25:1 to 1:25 | 5:1 to 1:5 | 3:1 to 1:3 |

The active substance combinations are well tolerated by plants, have favorable toxicity to warm-blooded species and are suitable for controlling stink bugs (family Pentatomidae) in soybeans, maize, rice, cereals (wheat, barley, rye, oats, triticale) and cotton.

The control of stink bugs (Pentatomidae) in soybeans is especially preferred.

The following are preferred from the stink bug family (Pentatomidae): *Antestiopsis* spp., *Dichelops* spp., *Euryga-ster* spp., *Euschistus* spp., *Nezara* spp., *Oebalus* spp., *Piezodorus* spp. and *Scothinophora* spp. in crops such as, for example, cereals, rice, maize, cotton and soybeans.

According to the invention, all plants and plant parts may be treated. In the present context, plants are understood as meaning all plants and plant populations, such as desired and undesired wild plants or crop plants (including naturally occurring crop plants). Crop plants may be plants which can be obtained by traditional breeding and optimization methods or by biotechnological and recombinant methods or by combinations of these methods, including the transgenic plants and including the plant varieties capable or not of being protected by Plant Breeders' Rights. Plant parts are to be understood as meaning all aerial and below-ground parts or organs of the plants, such as shoot, leaf, flower and root, with leaves, needles, stalks, stems, flowers, fruiting bodies, fruits and seeds, and roots, tubers and rhizomes being mentioned by way of example. The plant parts also include harvested material and vegetative and generative propagation material, for example cuttings, tubers, rhizomes, slips and seeds.

The treatment according to the invention of the plants and plant parts with the active substance combination is carried out directly or by acting on their environment, habitat or store by the customary treatment methods, for example by immersing, spraying, vaporizing, misting, dusting, painting on, injecting and, in the case of propagation material, in particular seeds, furthermore by coating with one or more coatings.

As has already been mentioned above, all plants and their parts may be treated in accordance with the invention. In a preferred embodiment, plant species and plant varieties, and their parts, which are found in the wild or which are obtained by traditional biological breeding methods such as hybridization or protoplast fusion, are treated. In a further preferred embodiment, transgenic plants and plant varieties, and their parts, which have been obtained by recombinant methods, if appropriate in combination with traditional methods (genetically modified organisms), are treated. The terms "parts" and "parts of plants" or "plant parts" have been detailed above.

It is especially preferred to treat, in accordance with the invention, plants of the plant varieties which are in each case commercially available or in use. Plant varieties are understood as meaning plants with new properties ("traits") which have been obtained by conventional cultivation, by mutagenesis or else by recombinant DNA techniques. These may be cultivars, biotypes or genotypes.

Depending on the plant species or plant varieties, their location and growth conditions (soils, climate, vegetation period, nutrition), the treatment according to the invention may also result in superadditive ("synergistic") effects. Thus, for example, reduced application rates and/or widenings of the activity spectrum and/or an increase in the activity of the substances and compositions that can be used according to the invention, better plant growth, increased tolerance to high or low temperatures, increased tolerance to drought or to water or soil salinity, increased flowering performance, easier harvesting, accelerated maturation, higher yields, better quality and/or a higher nutritional value of the harvested products, better storage stability and/or processability of the harvested products which exceed the effects which were actually to be expected are possible.

The preferred transgenic plants or plant varieties (i.e. those obtained by genetic engineering) which are to be treated according to the invention include all plants which, by recombinant modification, received genetic material which imparted particularly advantageous useful properties ("traits") to these plants. Examples of such properties are better plant growth, increased tolerance to high or low temperatures, increased tolerance to drought or to water or soil salinity, increased flowering performance, easier harvesting, accelerated maturation, higher yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidal active substances. Examples of transgenic plants which may be mentioned are the important crop plants, such as cereals (wheat, rice), maize, soybeans, potatoes, cotton, tobacco, oilseed rape and also fruit plants (with the fruits apples, pears, citrus fruits and grapes), and particular emphasis is given to maize, soybeans, potatoes, cotton, tobacco and oilseed rape. Traits that are emphasized in particular are the increased defense of the plants against insects, arachnids, nematodes, slugs and snails as the result of toxins formed in the plants, in particular those formed in the plants by the genetic material from *Bacillus Thuringiensis* (for example by the genes CryIA(a), CryIA(b), CryIA(c), CryIIA, CryIIIA, CryIIIIB2, Cry9c, Cry2Ab, Cry3Bb and CryIF and also combinations thereof) (hereinbelow referred to as "Bt plants"). Traits which are also particularly emphasized are the increased defense of plants against fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidal active substances, for example imidazolinones, sulfonylureas, glyphosates or phosphinothricin (for example the "PAT" gene). The genes which impart the desired traits in question can also be present in combinations with one another in the transgenic plants. Examples of "Bt plants" which may be mentioned are maize varieties, cotton varieties, soybean varieties and potato varieties which are sold under the trade names YIELD GARD® (for example maize, cotton, soybeans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soybean varieties which are sold under the trade names Roundup Ready® (tolerance to glyphosates, for example maize, cotton, soybeans), Liberty Link® (tolerance to phosphinothricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned also include the varieties sold under the name Clearfield® (for example maize). Of course, these statements also apply to plant varieties having these genetic traits or genetic traits which will be developed in the future, which varieties will be developed and/or marketed in the future.

The active substance combinations can be converted into the customary formulations, such as solutions, emulsions, wettable powders, suspensions, powders, dusts, pastes, soluble powders, granules, suspoemulsion concentrates, natural materials impregnated with active substances, synthetic materials impregnated with active substances and microencapsulations in polymeric materials.

These formulations are produced in a known manner, for example by mixing the active substance with extenders, that is, liquid solvents and/or solid carriers, optionally with the use of surface-active agents, that is, emulsifiers and/or dispersants and/or foam formers.

Suitable extenders are, for example, water, polar and unpolar organic chemical fluids, for example from the classes of the aromatic and nonaromatic hydrocarbons (such as paraffins, alkylbenzenes, alkylnaphthalenes, chlorobenzenes), of the alcohols and polyols (which may optionally also be substituted, etherified and/or esterified), of the ketones (such as acetone, cyclohexanone), esters (also fats and oils) and (poly) ethers, of the unsubstituted and substituted amines, amides, lactams (such as N-alkylpyrrolidones) and lactones, of the sulfones and sulfoxides (such as dimethyl sulfoxide).

If water is used as extender, auxiliary solvents which can also be used are, for example, organic solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol and ethers and esters thereof, ketones, such as acetone, methyl ethyl ketone, methyl isobutyl ketone or cyclohexanone, strongly polar solvents, such as dimethylformamide and dimethyl sulfoxide, and water.

As solid carriers there are suitable:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; as emulsifiers and/or foam formers there are suitable: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolysates; as dispersants there are suitable: for example lignosulfite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95% by weight of active substance, preferably between 0.5 and 90% and also, preferably, extenders and/or surface-active agents.

The active substance content of the use forms prepared from the commercially available formulations may vary within wide limits. The active substance concentration of the use forms can be from 0.0000001 up to 95% by weight of active substance, preferably between 0.0001 and 1% by weight.

The application is effected in a customary manner adapted to suit the use forms.

The plants mentioned can be treated particularly advantageously in accordance with the invention using the active substance mixture according to the invention. The preferred ranges indicated above for the mixtures also apply to the treatment of these plants. The treatment of plants with the mixtures specifically mentioned in the present text should be especially emphasized.

The good insecticidal activity of the active substance combinations according to the invention can be seen from the examples which follow. While the individual active substances show weaknesses in their activity, the combinations show an activity which exceeds a simple additive effect.

A synergistic effect in insecticides is always present when the activity of the active substance combinations exceeds the sum of the activities of the active substances applied individually.

The expected activity for a given combination of two active substances can be calculated as described by S. R. Colby, Weeds 15 (1967), 20-22, as follows:

If
X is the kill efficiency expressed in % of the untreated control when using active substance A at an application rate of m g/ha or a concentration of m ppm,
Y is the kill efficiency expressed in % of the untreated control when using active substance B at an application rate of n g/ha or a concentration of n ppm, and
E is the kill efficiency expressed in % of the untreated control when using active substances A and B at application rates of m and n g/ha or a concentration of m and n ppm,
then $$E = X + Y - \frac{X \cdot Y}{100}$$

If the actual insecticidal kill efficiency is greater than calculated, then the combination is superadditive in its kill efficiency, i.e. a synergistic effect is present. In this case, the kill efficiency actually observed must be greater than the value for the expected kill efficiency (E) calculated with the abovementioned formula.

After the desired period of time, the kill efficiency is determined in %. Here, 100% means that all animals have been killed; 0% means that no animals have been killed.

USE EXAMPLES

Stink Bugs (Pentatomidae)
Very especially preferred is the control of the following species from the stink bug family (Pentatomidae)

| | |
|---|---|
| *Antestiopsis orbitalus* | in soybeans |
| *Dichelops furcatus* | in maize, soybeans and cereals |
| *Dichelops melacanthus* | |
| *Eurygaster intergriceps* | in cereals |
| *Eurygaster maura* | |
| *Euschistus heros* | in cotton, rice and soybeans |
| *Euschistus servus* | |
| *Nezara hilare* | in cereals, cotton, soybeans and rice |
| *Nezara viridula* | |
| *Oebalus mexicana* | in rice and cereals |
| *Oebalus poecilus* | |
| *Oebalus pugnase* | |
| *Piezodorus guildinii* | in soybeans, rice and cotton |
| *Scotinophara lurida* | in rice |
| *Scotinophara coaretata* | |

Example 1

Plots approximately 58 m² in size and planted with soybean plants (Glycine max) cv. "BRS232" (growth stage 75) are treated in three replications against the brown stink bug (*Euschistus heros*), using a pneumatic sprayer. A mixture of the active substance (1-2) and imidacloprid (SC 480) is applied in comparison with the active substance (I-2) (SC 240) on its own and imidacloprid (SC 200) on its own at the application rates specified, as a tank mix with 0.1% a.i. methylated soya oil (EC 850). Methamidophos (SL 600) was tested concomitantly as commercially available standard. The water application rate is 200 l/ha. The evaluation is performed 14 days after the treatment by determining the kill efficiency of the nymphs.

| Active substance | Application rate g a.i./ha | Kill efficiency as calculated by Abbott (%) 14 d |
|---|---|---|
| Imidacloprid | 72 | 21 |
| Active substance (I-2) | 24 | 33 |
| Imidacloprid + Active substance (I-2) | 72 + 24 | 70 |
| Calculated using Colby's formula: | | 47.1 |
| Methamidophos | 480 | 27 |

Example 2

Plots approximately 1 m² in size, provided with cages and planted with soybean plants (*Glycine max*) cv. "CO-32" are treated in four replications against the red-banded stink bug (*Piezodorus guildinii*) using a pneumatically operated backpack sprayer. A mixture of the active substance (I-2) and imidacloprid (SC 480) is applied in comparison with the active substance (I-2) (SC 240) on its own and imidacloprid (SC 200) on its own at the application rates specified, as a tank mix with 0.1% a.i. methylated soya oil (EC 850). Methamidophos (SL 600) was tested concomitantly as commercially available standard. The water application rate is 300 l/ha. The evaluation is performed 1 and 3 days after the treatment by determining the kill efficiency of the adults.

| | | Kill efficiency as calculated by Abbott (%) | |
|---|---|---|---|
| Active substance | Application rate g a.i./ha | 1 d | 3 d |
| Imidacloprid | 70 | 65 | 65 |
| Active substance (I-2) | 24 | 0 | 27.5 |
| Imidacloprid + Active substance (I-2) | 72 + 24 | 90 | 90 |
| Calculated using Colby's formula: | | 65 | 74.6 |
| Methamidophos | 480 | 52.5 | 87.5 |

We claim:

1. A method for controlling insects from the stink bug family (Pentatomidae), comprising treating a plant, its parts, its environment, its habitat or its store with an active substance combination comprising a compound of formula (I-2)

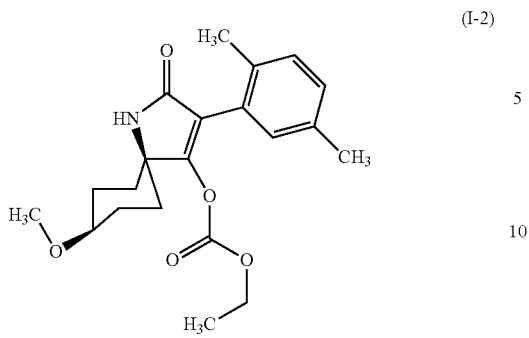

and imidacloprid, wherein said plant, its parts, its environment, its habitat or its store contains insects from the stink bug family.

2. The method according to claim 1, wherein the plant is selected from the group consisting of a maize plant, a rice plant, a soybean plant, a cotton plant or a cereal plant.

3. The method according to claim 2, wherein the plant is a soybean plant.

4. The method according to claim 2, wherein the plant is a maize plant.

5. The method according to claim 2, wherein the plant is a rice plant.

6. The method according to claim 2, wherein the plant is a cotton plant.

7. The method according to claim 2, wherein the plant is a cereal plant.

* * * * *